(12) United States Patent
Boldrini et al.

(10) Patent No.: US 7,321,000 B2
(45) Date of Patent: Jan. 22, 2008

(54) OPHTHALMIC COMPOSITION CONTAINING N-ACETYL-CYSTEINE FOR THE TREATMENT OF DRY-EYE SYNDROME

(75) Inventors: Enrico Boldrini, Pisa (IT); Marco Fabrizio Saettone, Pisa (IT); Patrizia Chetoni, Pisa (IT); Susi Burgalassi, Pisa (IT); Boris Giannaccini, Pisa (IT)

(73) Assignee: Farmigea S.p.A., Pisa (IT)

( * ) Notice: Subject to any disclaimer, the term of this patent is extended or adjusted under 35 U.S.C. 154(b) by 0 days.

(21) Appl. No.: 10/484,241

(22) PCT Filed: Jul. 22, 2002

(86) PCT No.: PCT/IT02/00481

§ 371 (c)(1),
(2), (4) Date: Jun. 30, 2004

(87) PCT Pub. No.: WO03/011249

PCT Pub. Date: Feb. 13, 2003

(65) Prior Publication Data

US 2004/0248847 A1 Dec. 9, 2004

(30) Foreign Application Priority Data

Jul. 23, 2001 (IT) .................. RM2001A0438

(51) Int. Cl.
*A61K 31/195* (2006.01)

(52) U.S. Cl. .................... 514/566; 514/912
(58) Field of Classification Search .......... 514/59, 514/912
See application file for complete search history.

(56) References Cited

U.S. PATENT DOCUMENTS 5,256,420 A * 10/1993 Tsao et al. ............... 424/427

FOREIGN PATENT DOCUMENTS

| EP | 0 551848 A1 | 7/1993 |
| IT | 1 151 755 B | 12/1986 |

* cited by examiner

*Primary Examiner*—Zohreh Fay
(74) *Attorney, Agent, or Firm*—Arent Fox LLP

(57) ABSTRACT

An ophthalmic pharmaceutical composition containing acetylcysteine as the active ingredient having a mucolitic action, suitable for administration in eyedrops, where N-acetyl-cysteine is neutralised with base DEAE-dextrane in order to reach pH levels preferably between 6.0 and 7.5, and having a physiologically acceptable osmolarity less than 320 mOsm/kg. The presence of a neutralising agent for N-acetyl-cysteine that does not negatively affect the composition osmolarity allows the formulation to be isotonic or even hypotonic, thus avoiding the irritative and potentially damaging effects of previous ophthalmic products containing N-acetyl-cysteine.

8 Claims, 2 Drawing Sheets

Figure 1:
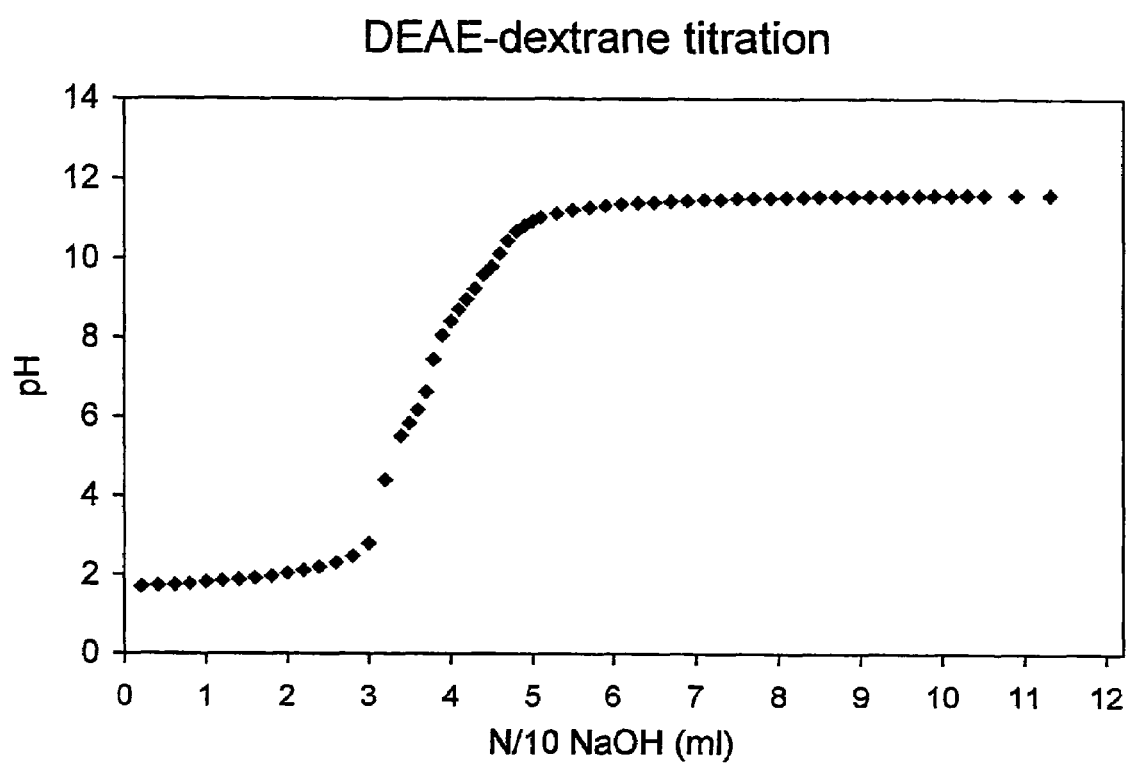

OPHTHALMIC COMPOSITION CONTAINING N-ACETYL-CYSTEINE FOR THE TREATMENT OF DRY-EYE SYNDROME

CROSS-REFERENCE TO RELATED APPLICATION

This application is a National Stage entry of International Application No. PCT/IT02/00481, filed Jul. 22, 2002, the entire specification claims and drawings of which are incorporated herewith by reference.

DESCRIPTION

The present invention relates to an ophthalmic composition containing N-acetyl-cysteine for the treatment of dry-eye syndrome. More particularly, the invention concerns compositions containing N-acetyl-cysteine as an active ingredient, which are suitable for topical administration in eyedrops because they are isotonic with the lacrimal fluid thanks to the presence of a neutralising agent for N-acetyl-cysteine that has no adverse effects on the osmolarity of the composition.

As is known, preocular tear film is an organised liquid structure covering the conjunctiva and the exposed surface of the eyeball. Under normal conditions, the tear film appears as a complex three-layered structure, consisting of:

- an internal mucous layer, composed of a glycoprotein mixture (mucin) produced by specialised cells (goblet cells) present in the conjunctival epithelium—this layer adheres to the corneo-conjunctival epithelium forming a hydrophilic surface.
- an abundant intermediate aqueous layer, overlaying the aforesaid hydrophilic surface, rich in oxygen and essentially composed of water, electrolytes, proteins, enzymes and mucin, that has a trophic, defence, vehicular and optical function.
- a thin external lipid layer that mainly acts to regulate the evaporation rate of water from the tear film.

The aforesaid three-layered structure constitutes a complex physiological structure whose main functions are those of protecting the eye surface, maintaining the hydration, lubrication and cleanliness of the corneal surface, and cooperating in producing proper eye-sight. The perfect equilibrium and continuous renewal of this physiological system is a necessary condition for it to fulfil its functions. For this to occur, there must firstly be a constant but not excessive water evaporation from lacrimal fluid, such that it maintains osmolarity around a physiological value of 300 mOsm/kg, and the tear film must be continuously redistributed on the corneal surface through blinking.

Various pathological or anomalous situations of the eye appear through discontinuity or alterations of the tear film, as a result, for example, of an inadequate blinking rate, prolonged use of contact lenses, the use of certain systemic pharmaceutical drugs or of senile hyposecretion. In this context, the term "dry-eye syndrome" is taken to mean a set of pathological manifestations of the ocular area characterised by the reduction and/or altered composition of the tear film, while more appropriately the characteristic alterations of the corneal surface that are produced in this way are identified with the term keratoconjunctivitis sicca. As may be self-evident, dry eye is a clinical disorder that is difficult to define as regards frequency because it is not always recognised due to its often bland and aspecific symptomatology and objectivity (Lemp M. A., Recent developments in dry eye management, *Opthalmology* 10, 1299-304 (1987); Lemp M. A., Dry eye syndromes: treatment and clinical trials. *Adv. Exp. Med. Biol.*, 350 553-9 (1994); Lemp M. A., Epidemiology and classification of dry eye, *Adv. Exp. Med. Biol.*, 438, 791-803 (1998)). A patient with dry-eye syndrome presents disorders such as conjunctival reddening, difficulty in opening eye-lids on awakening, a burning, prickling and sandy sensation, a feeling of a foreign body and also photophobia. Possible complications range from keratopathy with surface disepithelisation to infective keratitis and even serious infective degenerative pathologies of the cornea.

From a diagnostic standpoint, besides an evaluation of its own kind of symptoms, dry-eye syndrome may be identified and monitored through consolidated procedures, the most common being the measurement of tear production (the Schirmer test), tear film break-up time (BUT) after blinking and an evaluation of eye surface staining using rose bengal or fluorescein. Moreover, the value of tear osmolarity may be taken as an objective parameter of the pathological state under examination, it being demonstrated that in pathological conditions this value increases by 30-40 mOsm/kg on average.

The possible etiological factors are many. It is sometimes not possible, even with laboratory investigations and sophisticated equipment, to recognise the cause of this syndrome; in this case, one talks in terms of an "essential form", which is treatable exclusively as a symptom. In view of the fact that tear film alterations may have different pathological interpretations and therapeutical approaches depending on the type of the lacrimal component that is found altered, a fundamental step consists of assessing whether the anomaly is located in the lipid surface component, in the aqueous layer or in the internal mucinic one (Miglior M., Troiano P., Lacrimal film pathologies: classification and rationale of the therapy, in *Symposium on the Lacrimal System*, Toronto, Jun. 25, 1994, ed. Hurwitz J. et al., Kugler & Ghedini Publ., (1995)), to then draw the more appropriate conclusions from a therapeutic standpoint.

The alteration of the external lipid component, that is not per se a very frequent case, is usually due to a blepharitis, and must be treated as such. In the more frequent case that the intermediate aqueous layer is altered, this alteration always consists of a quantitative reduction of this component, linked to excessive evaporation, that leads to the aforesaid increase in lacrimal osmolarity. In this case particular compositions in eyedrops are indicated, known as "artificial tears", in formulations rich in water and with few or no mucomimetic agents, possibly associated with low hydration corneal contact lenses.

When the alteration is in the internal mucin layer, then the case is particularly delicate. It is known that the integrity of the mucin layer is one of the essential factors in maintaining tear film stability because the mucin improves the wettability of the corneal surface, allows the aqueous film to continuously and homogeneously adhere to the exposed surface, assuring stability, and increases the fluid phase viscosity, preventing too rapid a flow from the conjunctival sac.

As regards the mucin layer alterations, it has been reported (Miglior M. et al., loc. cit.) that they may appear with either a mucus deficit or an excess. When mucin is absent or insufficient, the cornea becomes unwettable and, due to the imbalance between the electrolytes and glycoproteins present, the tear film becomes unstable and can break up, thus producing dry areas. In the second case, an excess of mucin coagulates into threads that still hinder ocular surface wettability and leads to the formation of dry areas and to damage to the corneal epithelium. In this situation, too, it is possible to intervene at a topical ocular level by using suitably formulated "artificial tears" additioned with appropriate integrators of the mucin component and mucomimetic agents (namely, various cellulose derivatives, polyvinyl derivatives such as polyvinyl-pyrrolidone and polyvinyl alcohol, various polysaccharides and their derivatives, such as dextrane, hyaluronic acid, chondroitin sulfate, etc.) or, in case of an excess of the mucin component, using mucolitic agents such as N-acetyl-cysteine.

More specifically, for lacrimal mucous reduction and fluidification, N-acetyl-cysteine is mainly prescribed both for topical and systemic administration. Alternatively, other mucolytics can be used, such as carboxymethyl cysteine, bromhexine and ambroxol (the latter two with also a not better defined secretion-stimulating action) for systemic administration. The first of the aforesaid active ingredients, having the following structural formula,

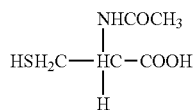

is a derivative of the natural amino acid L-cysteine that proves to be clinically useful as a mucolitic agent in acute and chronic bronchopulmonary pathologies, and is thus mainly prescribed for these disorders, mostly using a systemic administration. This molecule is considered to exert its activity by "breaking up" the disulfide (S—S) bonds of the mucus, thus reducing its viscosity. In the eye, N-acetyl-cysteine solutions can dissolve the mucus threads thereby reducing lacrimal viscosity.

N-acetyl-cysteine (also referred to hereinafter as N-AC) is a relatively strong acid and cannot be directly applied to the ocular surface as such, but only after being suitably neutralised. For example, a 4% weight N-AC aqueous solution has a pH of 1.90, and before it can be used in eyedrops, the acid form must be neutralised, for example with NaOH, in order to yield the corresponding sodium salt and to bring the pH within a range that is physiologically tolerated by the human eye. However, the necessary neutralisation has the drawback of increasing the osmolarity of the resulting solution that goes from an original value of 241 mOsm/kg to values corresponding to high hypertonicity. In this regard, Italian patent No. 1151755 (Bruschettini s.r.l.) describes an eyedrop composition containing N-AC, where the active ingredient is supplemented with a disodium phosphate buffer and an amount of sodium bicarbonate sufficient to bring the pH of the solution within the range 6.6-7.0. Even though the document does not highlight any resulting inconveniences in tolerability, it presents hypertonicity as a fundamental characteristic of the proposed formulation.

Another N-acetyl-cysteine based formulation for topical ophthalmic use is described in EP-A-0 551 848 (Zambon Group S.p.A.), in which the N-AC solution, preferably 4% weight, is associated with polyvinyl alcohol in order to obtain a product of improved activity for the treatment of keratoconjunctivitis sicca. In this case, the document does not report the osmolarity values presented by the proposed formulations, but it is clear from the corresponding compositions that they are strongly hypertonic formulations.

Actually, currently commercially available N-AC-based eyedrops pre-sent much higher osmolarity values than the "physiological" value of 300 mOsm/kg. These values are >1000 mOsm/kg for the product marketed under the Brunac® tradename (Bruschettini s.r.l., containing 5% N-AC), and around 900 mOsm/kg for the Tirocular® product (ACRAF S.p.A, containing 4% N-AC). As previously pointed out as regards the importance of avoiding excessive tear film hypertonicity, it is obvious that the aforesaid formulations may be irritating and potentially damaging to the corneal surface. This is all the more so if it is considered that lacrimal fluid of patients with dry-eye syndrome is already hypertonic and thus the relative treatment must not aggravate these conditions by administering hypertonic preparations. It is for these very considerations that artificial tears are produced in isotonic or, preferably, hypotonic formulations (Holly F. J., Lamberts D. W., Effect of nonisotonic solutions on tear film osmolality. *Invest. Opthalmol. Vis. Sci.*, 20, 236 (1981)).

Considering also the possibility of neutralising acetylcysteine with organic bases other than an inorganic NaOH base, strongly hypertonic solutions are still obtained, as the following examples show.

Neutralisation with Sodium Hydrate

| | |
|---|---|
| N—AC | 5.00 g |
| Viscosity enhancing polymer | 1.00 g |
| NaOH | 1.18 g |
| Sterile dist. $H_2O$ | q.s. to 100 ml |
| pH = 7.00; | Osmolarity = 644 mOsm/kg |

Neutralisation with L-lisine

| | |
|---|---|
| N—AC | 5.00 g |
| L-lisine | 4.50 g |
| Sodium edetate | 0.10 g |
| Viscosity enhancing polymer | 2.00 g |
| Sterile dist. $H_2O$ | q.s. to 100 ml |
| pH = 7.00; | Osmolarity = 620 mOsm/kg |

Neutralisation with L-arginine

| | |
|---|---|
| N—AC | 5.00 g |
| L-arginine | 6.20 g |
| Sodium edetate | 0.10 g |
| Viscosity agent polymer | 2.00 g |
| Sterile dist. $H_2O$ | q.s. to 100 ml |
| pH = 7.00; | Osmolarity = 656 mOsm/kg |

Neutralisation with L-istidine

| | |
|---|---|
| N—AC | 4.00 g |
| L-istidine | 8.00 |
| Sterile dist. $H_2O$ | q.s. to 100 ml |
| pH = 6.50; | Osmolarity = 409 mOsm/kg |

Neutralisation with L-methylglucamine

| | |
|---|---|
| N—AC | 4.00 g |
| L-methyl-glucamine | 3.40 g |
| Sterile dist. $H_2O$ | q.s. to 100 ml |
| pH = 7.30; | Osmolarity = 490 mOsm/kg |

Neutralisation with L-glycine Sodium Carbonate

| N—AC | 4.00 g |
|---|---|
| L-glycine sodium carbonate | 3.60 g |
| Sterile dist. H$_2$O | q.s. to 100 ml |
| pH = 7.20; | Osmolarity = 1636 mOsm/kg |

Neutralisation with L-glucamine

| N—AC | 4.00 g |
|---|---|
| L-glucamine | 4.80 g |
| Sterile dist. H$_2$O | q.s. to 100 ml |
| pH = 7.30; | Osmolarity = 631 mOsm/kg |

The foregoing examples show that commonly used pharmaceutical neutralisers lead to considerably hypertonic formulations in cases of 5.0% or 4.0% N-acetyl-cysteine, and both in the presence or absence of a viscosity enhancing polymer.

In view of the above, it is an object of the present invention to provide an acetylcysteine-based pharmaceutical composition for topical ophthalmic use which can be advantageously used in mucolitic active preparations for the treatment of dry-eye syndrome without presenting the drawbacks of poor tolerability or toxicity for ocular tissues normally linked to low pH values and, above all, to osmolarity values much higher than physiological ones. More specifically, the ophthalmic preparation—although exploiting the mucolitic properties of acetylcysteine—must be chemically close to neutrality and, at the same time, be isotonic or, preferably, hypotonic.

To this end, the present invention proposes neutralising the acetylcysteine with a base agent that, although positively contributing to the overall performance of the formulation as an artificial tear, also poorly contributes to tonicity, thus allowing to obtain N-AC solutions which are isotonic, or even hypotonic, with lacrimal fluid.

Within the frame of the studies that have led to the present invention, it has been found that a polycationic derivative of dextrane, diethylaminoethyl-dextrane (DEAE-dextrane), containing diethylaminoethyl groups linked to the glucose moieties of the dextrane skeleton through ether bonds that are exceptionally stable to acid hydrolysis, is surprisingly effective in neutralising the acidity of N-acetyl-cysteine by forming its corresponding salt, without appreciably contributing to the tonicity of the resulting solution. At the same time, the formulation obtained by neutralising N-AC with the polycationic derivative of dextrane already incorporates a viscosity enhancing polymer whose presence, as already noted, is advantageous in a great many disorders linked to dry-eye syndrome.

DEAE-dextrane, which is already known and used in medicine for the treatment of hypercholesterolemy and as an antilipermic in general (U.S. Pat. Nos. 3,627,872 and 4,160,826), is obtained by reacting 2-chloroethyl-diethylamine, in an alkaline solution, with dextrane—a polysaccharide whose structure formula may be illustrated as follows:

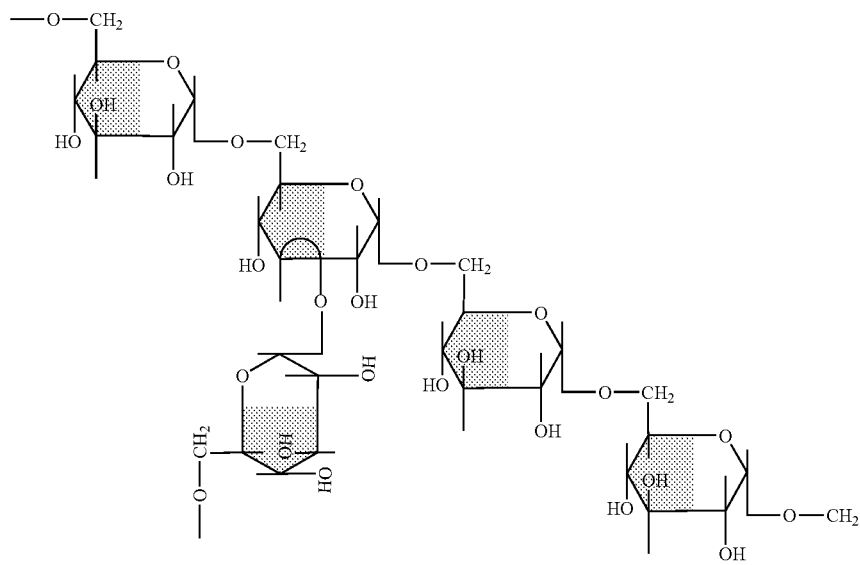

As the starting polysaccharide, the diethylaminoethyl derivative is composed of glucopyranose units linked mainly through 1→6 bonds, while a small number of 1→3 bonds (and, to a lesser extent, 1→2 and 1→4 bonds) are responsible for the side branching. The average molecular weight is about 500,000 and the nitrogen content is approximately 3.2%, which corresponds to one cation group for every three glucose units. Similarly to dextrane sulphate, DEAE-dextrane is a polyelectrolyte and its properties differ considerably from the starting polymer—dextrane.

Being a polycationic product, DEAE-dextrane is normally commercially available in the salified form of the corresponding chloride or sulphate. The free base form, necessary as a starting reagent for neutralising N-acetyl-cysteine as proposed according to the present invention, may be prepared, for example, from DEAE-dextrane chloride (or sulfate) by treating with ionic exchange resins, according to the following method.

A ionic exchange resin (DOWEX 1×8, 30 ml) is packed in a column and treated with 0.1N NaOH in order to hydrate and activate it. Next, 1N NaOH is made to pass through the resin. The resin is then washed at length in water to eliminate the excess NaOH and a 5% DEAE-dextrane HCL solution is introduced in the column. The solution in the column, containing base DEAE-dextrane, is concentrated by reduced pressure evaporation and then dried.

Figure 2:
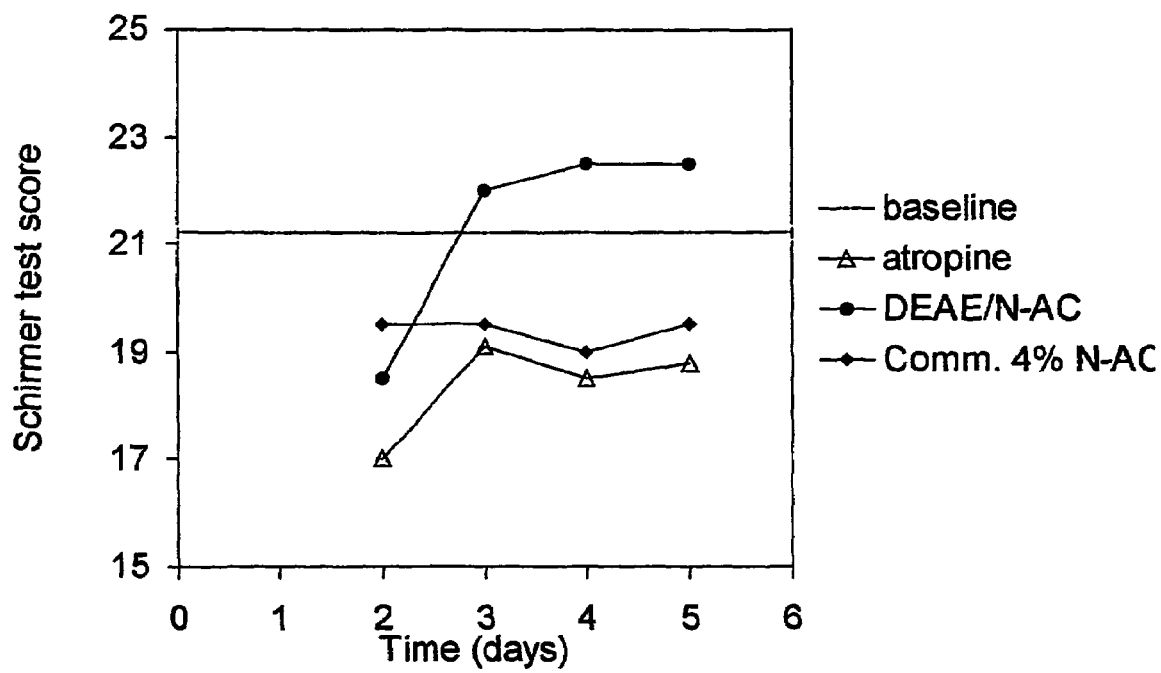
Figure 3:
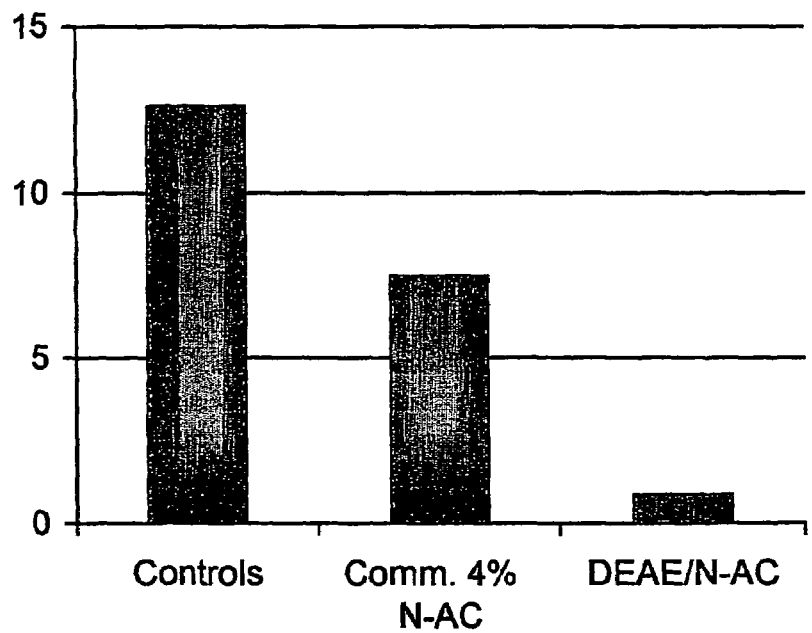

To determine the neutralising capacity of N-acetyl-cysteine with which it must be formulated, the product in a free base form as obtained, if required, from the previous operation is titrated with 0.1N HCl. This operation, which allows a preventive determination of the number of chemical equivalents contained in the mass unit of the neutralising agent, may be carried out, for example, by a "return titration" in which to a certain quantity of base DEAE-dextrane dissolved in distilled water is first added an excess of strong acid (HCl) and then the excess strong acid is titrated with a strong base (NaOH). The pH values, measured via potentiometrically), obtained with this operation, are reported in one of the attached diagrams. By way of example and with reference to certain specific embodiments of the invention, FIG. 1 shows a titration curve of the base DEAE-dextrane used in the composition of the present invention;

FIG. 2 shows the results of the Schirmer test in an evaluation of the activity of the composition in an experimental model of dry-eye syndrome in rabbit; and FIG. 3 shows the results of the observation via slit lamp of the cornea after staining with sodium fluorescein in the same experimental model in rabbit.

Temporarily leaving aside the two figures concerning the application experimentation of the compositions of the invention, that will be dealt with later on, and returning to the base DEAE-dextrane titration, FIG. 1 shows the potentiometric curve obtained when using the aforesaid procedure to treat 0.08 g of base DEAE-dextrane dissolved in 5 ml of distilled water, to which was added 5.0 ml of N/10 HCl. The potentiometric titration of the excess HCl with NaOH, in which the pH values progressively obtained are indicated in the diagram, showed that the flexion point at pH 7.0 is reached after adding 3.6 ml of basic solution. Therefore, 1.4 ml (5.0-3.6) of N/10 HCl, i.e. 0.14 mEq, neutralised 0.08 g of base DEAE-dextrane. This allows assessing the equivalent weight of the polycationic reagent under study as 0.14/0.08=1.75 mEq/g.

In view of the above, it is thus possible to easily realise a N-AC-based formulation in which this active ingredient is neutralised by an appropriate proportion of base DEAE-dextrane that, as will be seen more clearly in the following examples, does not penalise the osmolarity of the composition but allows obtaining ophthalmic solutions that are also advantageously isotonic.

Therefore, the present invention specifically provides an ophthalmic composition based on acetylcysteine for administration in eyedrops, containing N-acetyl-cysteine neutralised with base DEAE-dextrane and having a physiologically acceptable osmolarity. More specifically, as is already known, said osmolarity is less than 320 mOsm/kg, and preferably less than 300 mOsm/kg, while the pH of the composition ranges between 6.0 and 7.5, and is preferably in the range 6.2-7.0. The osmolarity is preferably between 240 and 300 mOsm/kg. The above characteristics allow achieving solutions which may be administered in eyedrops suitable for the treatment of dry-eye syndrome—the solutions preferably containing from 3 to 5% weight N-acetyl-cysteine neutralised with a quantity of between 9% and 15% by weight of base DEAE-dextrane.

The formulations according to the present invention are conveniently prepared as either a solution or an aqueous suspension in a pharmaceutically acceptable ophthalmic vehicle, and may contain one or more of the other possible ingredients known in pharmaceutical technology for this kind of preparations. In particular, in addition to N-acetyl-cysteine and DEAE-dextrane, the formulations may also contain minor quantities of other viscosity enhancing polymers, such as the ones cited with reference to the prior art and of which some are reported in the example formulations below. As is customary, the compositions may contain further adjuvants, among which chelating agents, antimicrobials and preservatives, although the latter are normally avoided in eyedrop, if possible by using unitary dose packages without preservatives.

Some specific embodiments of the ophthalmic compositions according to the present invention, as well as some experimental data concerning the performance of these compositions and a comparison with the prior art, are reported in the following examples.

EXAMPLE 1

Taking into account the equivalent proportions already determined as previously described, a N-acetyl-cysteine and DEAE-dextrane based hypotonic preparation is produced with the following formulation:

| | |
|---|---|
| N—AC | 4.0 g |
| Base DEAE-dextrane | 12.0 g |
| Sterile dist. H$_2$O | q.s. to 100 ml |
| pH = 6.18; | Osmolarity = 245 mOsm/Kg |

For the preparation, 4 g of NAC is dissolved in about half the quantity of water available and 12 g of base DEAE-dextrane is dissolved in the remaining water. The two solutions are then combined and filtered using a 0.2 μm sterilising filter.

In addition to the aforesaid osmolarity value, the composition shows a viscosity of 21 mPa·s and a Newtonian type flow.

EXAMPLE 2

The hypotonic composition according to the invention in this case contains a preservative, according to the following formulation:

| | |
|---|---|
| N—AC | 4.0 g |
| Base DEAE-dextrane | 12.0 g |
| Benzalkonium chloride | 0.01 g |
| Sterile dist. H$_2$O | q.s. to 100 ml |
| pH = 6.23; | Osmolarity = 245 mOsm/kg |

For the preparation, N-AC, DEAE-dextrane and benzalkonium chloride are separately dissolved in distilled water. The solutions are then combined and filtered using a 0.2 μm sterilising filter.

If required, the osmolarity may be brought to a physiological value of 300 mOsm/kg by adding NaCl.

EXAMPLE 3

Taking into account the already determined equivalent proportions as described above, and proceeding for the preparation in a similar manner as the examples illustrated above, a N-acetyl-cysteine and DEAE-dextrane based hypotonic preparation is produced according to the following formulation:

| | |
|---|---|
| N—AC | 3.0 g |
| Base DEAE-dextrane | 9.0 g |
| Sterile dist. H$_2$O | q.s. to 100 ml |
| pH = 6.2; | Osmolarity = 185 mOsm/Kg |

EXAMPLE 4

A hypotonic but more concentrated preparation is obtained with a similar preparatory procedure, but with the following quantities:

| | |
|---|---|
| N—AC | 5.0 g |
| Base DEAE-dextrane | 15.0 g |
| Sterile dist. H$_2$O | q.s. to 100 ml |
| pH = 6.5; | Osmolarity = 307 mOsm/Kg |

Other formulation examples that show the optional presence of further viscosity enhancers, whose concentration generally ranges between 0.5 and 3% weight, are reported below. In all the cases, the procedure for the preparation is similar to the ones illustrated in the previous examples, and hypotonic products are obtained in all cases.

EXAMPLE 5

| | |
|---|---|
| N—AC | 4.0 g |
| Base DEAE-dextrane | 12.0 |
| Polyvinyl alcohol* | 0.5 |
| Sterile dist. H$_2$O | q.s. to 100 ml |

*Polyviol W 48/20, Wacker Chemie

EXAMPLE 6

| | |
|---|---|
| N—AC | 4.0 |
| Base DEAE-dextrane | 12.0 |
| Hydroxypropyl cellulose* | 0.4 |
| Sterile dist. H$_2$O | q.s. to 100 ml |

*Klucel MF, Aqualon Co.

EXAMPLE 7

| | |
|---|---|
| N—AC | 4.0 g |
| Base DEAE-dextrane | 12.0 |
| Hyaluronic acid* | 0.2 |
| Sterile dist. H$_2$O | q.s. to 100 ml |

*Hyalastine Fidia S.p.A.

EXAMPLE 8

| | |
|---|---|
| N—AC | 4.0 g |
| Base DEAE-dextrane | 12.0 |
| Polyvinylpyrrolidone* | 0.4 |
| Sterile dist. H$_2$O | q.s. to 100 ml |

*Kollidon PF 12, BASF

In order to assess the performance of the compositions according to the present invention, several experiments were carried out and some of the results are reported below.

Biocompatibility Studies

Biocompatibility studies were carried out in vivo with rabbit eyes by administering 50 µl of the formulation described in Example 2, at close intervals. No primary signs of irritation were found.

Stability Studies

The formulations underwent autoclaving (120° C., 20 min.): as highlighted in the prior art, N-acetyl-cysteine is degraded by about 30% (both in the presence and absence of benzalkonium chloride). It is, however, possible to carry out sterilisation by filtering through a 0.2 µm membrane, as was performed in the aforesaid examples.

Analytical Method Used for Determining N-AC in the Presence of DEAE-Dextrane

In order to evaluate the stability of N-AC in the vehicle, it is not possible to use the HPLC method or ultraviolet spectrophotometry. The following calorimetric method was thus employed (Raggi M. A., Cavrini V. and Di Pietra A. M., Colorimetric determination of acetylcysteine, penicillamine and mercaptopropionylglycine in pharmaceutical dosage forms, *J. Pharm. Sci.*, 71, 1384-1386 (1982)).

Reagents Used
  1, 10-phenantroline 0.25% (100 ml)
  Ferric solution 4×10$^{-3}$M (1000 ml)
  pH 4 acetate buffer (100 ml)
  Sodium acetate 0.2M (100 ml)

Reagent Preparation
  o-phenantroline 0,25%
  0.25 g of the compound is dissolved in distilled H$_2$O and after slight heating is then taken to the required volume with distilled H$_2$O. The solution is stored for three days in a dark glass container away from the light.
  Ferric Solution
  1.92 g of FeNH$_4$SO$_4$×12 H$_2$O is dissolved in distilled H$_2$O and then treated with 10 ml of concentrated HCl. It is taken to the required volume with distilled H$_2$O. The solution is stored for three days in a dark glass container away from the light.
  pH 4 buffer
  This is obtained by mixing 75 ml of 0.1M CH$_3$COOH with 25 ml of 0.1M CH$_3$COONa. If necessary, the pH may be adjusted with a solution of 0.2M CH$_3$COONa.

Standards Preparation
  0.163 g of acetylcysteine is dissolved in 500 ml of distilled H$_2$O. By diluting in a proportion of 1:5, the required concentration is obtained.
  Increasing volumes of this solution (1-5 ml) are placed in a 25 ml flask and then the following are added in succession:
  6 ml of ferric solution
  2.5 ml of o-phenantroline 0.25%
  3.5 ml of 0.2M NaOAc
  4.5 ml of pH4 buffer After 20 min the absorbance is measured at 515 nm by using as reference a control prepared at the same time as the sample.

The procedure described above was also applied to carry out the calibration of N-AC in the presence of DEAE-dextrane. For these samples, the measurement was carried out by using as reference a control containing the polymer and also a control without DEAE-dextrane. The spectra are comparable.

By comparing the spectrum obtained with N-AC with the one obtained for the samples also containing the polymer, it may be confirmed that DEAE-dextrane does not interfere with the adsorption, but it modifies its intensity.

Activity Studies in an Experimental Model of Dry-Eye Syndrome in the Rabbit.

The trials were carried out on a group of 10 New Zealand albino male rabbits weighing 2-2.5 kg and kept in standard conditions. The formulation of Example 2 (called DEAE/N-AC) was compared not only with controls that only received a physiological solution, but also with a commercially available (hypertonic) formulation containing 4% N-AC.

A drop of a solution of 1.0% atropine sulphate (AS) was administered in both eyes of the animals 3 times a day for 5 consecutive days in order to cause an experimental dry-eye condition (Burgalassi S., Panichi L., Chetoni P., Saettone M. F. and Boldrini E., Development of a simple dry eye model in the albino rabbit and evaluation of some tear substitutes, *Ophthalmic Res.* 31, 229-235 (1999)). 5 minutes after AS administration, 50 µl (corresponding to one drop) of one of the formulations under study or of a physiological solution (control group) was instilled in only the right eye.

At appropriate time intervals (2, 3, 4 and 5 days from the start of the treatment) the animals underwent the Schirmer test and an observation of the ocular surface, after staining with sodium fluorescein, by slit lamp with a cobalt blue filter.

The Schirmer test envisages the introduction of a strip of blotting paper of standard size and materials in the external third of the lower conjunctival fornix. The strip is left in place for a fixed period of time (3 min). The time taken for the lacrimal fluid to rise and the length in mm of the portion of paper wetted by the tears provide the score for lacrimal secretion. The test results obtained in the various treatment conditions are reported in FIG. 2. The vertical axis of the graph gives the millimeters of wetted strip in three minutes. The unbroken line (baseline) corresponds to the average physiological value, observed in the untreated animals (21,2 mm).

It may be noted that, in the eyes treated with a physiological solution (control group), there is a clear decrease in lacrimal secretions, that continues over the five days of observation. The Schirmer test scores for the hypertonic commercially available formulation do not greatly differ from those of the control group, except for the second day of observation. The formulation according to the present invention (DEAE/N-AC) instead produces better test scores, as of the third day, than baseline ones. The formulation thus seems capable of effectively contrasting the effects of decreased lacrimal production caused by atropine.

FIG. 3 shows the results obtained through the observation, via slit lamp, of the animals' cornea after staining with sodium fluorescein. This colouring highlights alterations (corneal lesions) produced by AS treatment, of the kind normally found in eyes with dry-eye syndrome. For each treatment, the values are expressed as a percentage of eyes in which intensely coloured dots were noted (correposnding to epithelial alterations of the cornea) with respect to the total number of eyes examined from the third to fifth day of treatment. As may be noted, unlike with the commercially available formulation, the formulation of Example 2 according to the present invention reduces the overall number of observed alterations practcally to zero.

The present invention has been disclosed with particular reference to some specific embodiments thereof, but it should be understood that modifications and changes may be made by the persons skilled in the art without departing from the scope of the invention as defined in the appended claims.

The invention claimed is:

1. An ophthalmic composition based on acetylcysteine for administration in eyedrops, containing from 3 to 5% by weight of N-acetyl-cysteine neutralized with from 9 to 15% by weight of base DEAE-dextrane and having a physiologically acceptable osmolarity of less than 320 mOsm/kg.

2. An ophthalmic composition according to claim 1 having an osmolarity below 300 mOsm/kg and a pH between 6.0 and 7.5.

3. An ophthalmic composition according to claim 1 wherein said pH is between 6.2 and 7.0.

4. An ophthalmic composition according to claim 1, in the form of a solution or an aqueous suspension in a pharmaceutically acceptable ophthalmic vehicle.

5. An ophthalmic composition according to claim 4, also containing other viscosity-enhancing polymers.

6. An ophthalmic composition according to claim 5 wherein said viscosity-enhancing polymers are selected from the group consisting of: polyvinyl alcohol, hydroxypropyl cellulose, hyaluronic acid, polyvinylpyrrolidone, chondroitin sulfate.

7. An ophthalmic composition according to claim 4 also containing preservatives, antimicrobials and/or chelating agents.

8. An ophthalmic composition according to claim 1, containing 4% by weight of N-acetyl-cysteine, 12% by weight of DEAE-dextrane, having a pH ranging between 6.2 and 7 and an osmolarity between 240 and 300 mOsm/kg.

* * * * *